United States Patent
Themelis

(10) Patent No.: US 12,156,769 B2
(45) Date of Patent: Dec. 3, 2024

(54) SURGICAL MICROSCOPE SYSTEM AND CORRESPONDING APPARATUS, METHOD AND COMPUTER PROGRAM

(71) Applicant: Leica Instruments (Singapore) Pte. Ltd., Singapore (SG)

(72) Inventor: George Themelis, Lindau (DE)

(73) Assignee: Leica Instruments (Singapore) Pte Ltd., Singapore (SG)

( * ) Notice: Subject to any disclaimer, the term of this patent is extended or adjusted under 35 U.S.C. 154(b) by 255 days.

(21) Appl. No.: 17/755,893

(22) PCT Filed: Oct. 30, 2020

(86) PCT No.: PCT/EP2020/080558
§ 371 (c)(1),
(2) Date: May 11, 2022

(87) PCT Pub. No.: WO2021/094110
PCT Pub. Date: May 20, 2021

(65) Prior Publication Data
US 2022/0378543 A1 Dec. 1, 2022

(30) Foreign Application Priority Data
Nov. 14, 2019 (EP) ..................................... 19209243

(51) Int. Cl.
*G08B 3/00* (2006.01)
*A61B 90/25* (2016.01)
(Continued)

(52) U.S. Cl.
CPC ............. *A61B 90/25* (2016.02); *F16M 11/12* (2013.01); *G02B 7/001* (2013.01);
(Continued)

(58) Field of Classification Search
CPC .......... A61B 90/25; A61B 2017/00017; A61B 2017/00119; A61B 2017/00199;
(Continued)

(56) References Cited

U.S. PATENT DOCUMENTS 5,480,114 A * 1/1996 Nakamura ............. A61B 90/50
359/384
5,667,186 A * 9/1997 Luber .................... G02B 7/001
248/550

(Continued)

FOREIGN PATENT DOCUMENTS

DE         4320443 C2   12/1994
DE         9321576 U1   12/1999
(Continued)

*Primary Examiner* — Toan N Pham
(74) *Attorney, Agent, or Firm* — 2SPL Patent Attorneys PartG mbB; Yong Beom Hwang

(57) ABSTRACT

Examples relate to a surgical microscope system and a corresponding apparatus, method and computer program. The surgical microscope system comprises one or more sensors for providing sensor information about a balance of the surgical microscope system. The surgical microscope system comprises one or more brakes for holding at least one component of the surgical microscope system in place. The surgical microscope system comprises a surgical microscope. The surgical microscope system comprises a processing module, configured to process the sensor information. The processing module is configured to determine an information about the balance of the surgical microscope system. In some embodiments, the processing module is configured to provide a warning to a user of the surgical microscope system based on the information about the balance of the surgical microscope system. The warning indicates danger of imbalance in the surgical microscope system. Alternatively or additionally, the processing module may be configured to control a release of the one or more brakes based (Continued)

Figure 1:
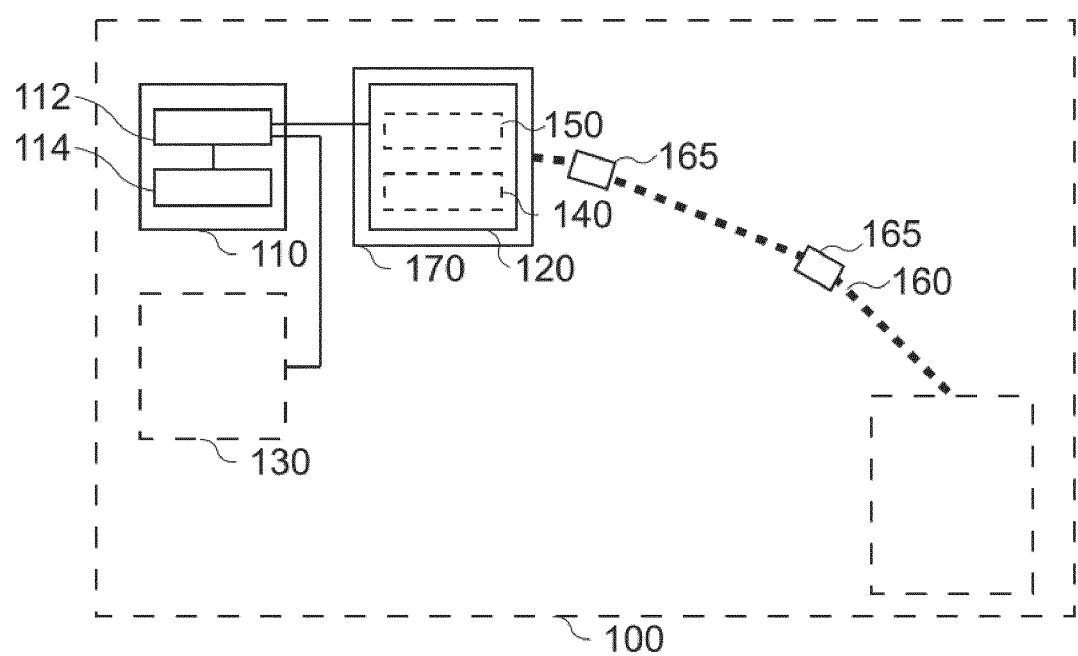

on the information about the balance of the surgical microscope system.

15 Claims, 2 Drawing Sheets

(51) Int. Cl.
  *F16M 11/12* (2006.01)
  *G02B 7/00* (2021.01)
  *G02B 21/00* (2006.01)
  *G08B 5/00* (2006.01)
  *G08B 7/00* (2006.01)
  *G08B 7/06* (2006.01)
  *G08B 21/18* (2006.01)
(52) U.S. Cl.
  CPC ........... *G02B 21/0012* (2013.01); *G08B 7/06* (2013.01); *G08B 21/18* (2013.01); *F16M 2200/041* (2013.01); *F16M 2200/066* (2013.01)
(58) Field of Classification Search
  CPC ........ A61B 2090/064; A61B 2090/067; A61B 34/76; A61B 90/50; A61B 2090/5025; A61B 2090/508; F16M 11/12; F16M 2200/041; F16M 2200/066; G02B 7/001; G02B 21/0012; G08B 7/06; G08B 21/18
  See application file for complete search history.

(56) References Cited

U.S. PATENT DOCUMENTS

| | | | | |
|---|---|---|---|---|
| 6,763,286 | B2* | 7/2004 | Metelski | F16M 11/2064 248/162.1 |
| 7,119,315 | B2* | 10/2006 | Klein | G02B 21/0012 250/201.3 |
| 8,416,492 | B2* | 4/2013 | Enge | G02B 21/24 359/368 |
| 2012/0184846 | A1* | 7/2012 | Izatt | G02B 21/0012 356/479 |
| 2019/0327394 | A1* | 10/2019 | Ramirez Luna | H04N 23/51 |

FOREIGN PATENT DOCUMENTS

| | | |
|---|---|---|
| DE | 102008011638 A1 | 9/2009 |
| EP | 1193438 A2 | 4/2002 |
| EP | 1326115 A1 | 7/2003 |
| EP | 1205703 B1 | 6/2006 |
| WO | 2015140241 A1 | 9/2015 |

* cited by examiner

SURGICAL MICROSCOPE SYSTEM AND CORRESPONDING APPARATUS, METHOD AND COMPUTER PROGRAM

TECHNICAL FIELD

Examples relate to a surgical microscope system and a corresponding apparatus, method and computer program.

BACKGROUND

Surgical microscopes systems are often designed so that an optical carrier (i.e. the surgical microscope) can be moved as easy and smoothly as possible, ideally giving the sense of lack of gravity. To achieve this, a balance of the optical carrier may be maintained through various means. However, the balance may be more difficult to obtain when accessories such as external cameras are added, or when components such as eyepieces are physically readjusted. To simplify the process or balancing, some microscopes offer an automatic balancing functionality. For example, patent documents EP 1326115 A1, DE 10 2008 011638 A1 and DE 4320443 C2 show such functionality. Using this functionality, the user might not be required to put effort nor spend time for balancing the microscope.

Although the balancing of the optics carrier can be achieved automatically, the auto-balancing function often relies on the user to sense the imbalance and trigger the auto-balancing function. For small imbalances, this might not be problematic, as the surgical microscope system may remain stable enough. However, at bigger imbalances, the surgeon may be surprised by a sudden movement of the surgical microscope system when they release the brakes of the arm hording the optics carrier, while expecting the optics carrier to remain in the same position.

There may be a desire for an improved surgical microscope system, in which an imbalance of the surgical microscope system is avoided or mitigated.

SUMMARY

Examples may relate to approaches for avoiding situations where the microscope moves abruptly due to imbalance. Embodiments are based on the finding that one or more sensors may be employed to obtain information about a balance of the surgical microscope. If a danger of imbalance is detected, a warning may be provided for a user of the surgical microscope system, enabling the user to take countermeasures, or a brake control may be overridden, avoiding situations in which a sudden movement occurs.

Embodiments of the present disclosure provide a surgical microscope system. The surgical microscope system comprises one or more sensors for providing sensor information about a balance of the surgical microscope system. The surgical microscope system comprises one or more brakes for holding at least one component of the surgical microscope system in place. The surgical microscope system comprises a surgical microscope. The surgical microscope system comprises a processing module, configured to process the sensor information. The processing module is configured to determine an information about the balance of the surgical microscope system. In some embodiments, the processing module is configured to provide a warning to a user of the surgical microscope system based on the information about the balance of the surgical microscope system. The warning indicates a danger of imbalance in the surgical microscope system. Alternatively or additionally, the processing module may be configured to control a release of the one or more brakes based on the information about the balance of the surgical microscope system. By determining the information on the balance based on the sensor information, an impending imbalance may be detected in time. Once the condition is detected, the user may be warned, or a brake release may be overridden, in order to avoid situations in which the surgical microscope system experiences a sudden movement.

In some embodiments, the processing module is configured to determine the information about the balance of the surgical microscope system in response to a release of one or more brakes of the surgical microscope system. This may provide a determination of the information about the balance at a point in time where a danger of imbalance is heightened.

Alternatively, the processing module may be configured to continuously determine the information about the balance of the surgical microscope system. This may provide a continuous monitoring of the balance of the surgical microscope system.

In at least some embodiments, the surgical microscope system comprises an output module for providing the warning for a user of the surgical microscope system. The warning may be provided via the output module. The user may be warned via the output module, and thus take action to correct the imbalance.

For example, the output module may comprise a light or a display. The warning may be provided as a visual warning. For example, the light or display may be placed in a field of view of the user/surgeon, so it can be perceived even if the user/surgeon is concentrated on their work.

Additionally or alternatively, the output module may comprise an audio output module. The warning may be provided as an audio warning. Thus, a warning may be provided without the surgeon/user having to turn their eyes away from the surgery.

Additionally or alternatively, the output module may comprise a haptic feedback actuator. The warning may be provided as haptic feedback. For example, the haptic feedback may be provided when the user/surgeon grabs handles of the surgical microscope.

In some embodiments, the processing module may be configured to dim or deactivate an illumination or a video display of the surgical microscope system as warning for the user of the surgical microscope system. In this case, existing output modules may be repurposed to provide the warning.

In various embodiments, the processing module is configured to at least partially and/or temporarily block a release of the one or more brakes based on the information about the balance of the surgical microscope system. This may limit a movement being performed by the surgical microscope, in order to avoid the surgical microscope system losing balance.

In some embodiments, the surgical microscope system may comprise an auto-balancing system for balancing the surgical microscope system. The warning may request the user to initiate the auto-balancing system. By activating the auto-balancing system, any imbalance may be corrected.

The one or more sensors may comprise one or more elements of the group of one or more torque sensors, one or more weight sensors, one or more accelerometers, one or more position sensors, one or more angular sensors, one or more rotation sensors. Various types of sensors or combinations of sensor may be sued to provide the information on the balance.

In some embodiments, the surgical microscope system may comprise an arm. The one or more brakes may be suitable for holding the arm in place. The surgical microscope may be attached to the arm. Determining the information about the balance of the surgical microscope system may comprise determining a velocity of a movement of the arm. For example, an imbalance may warrant a warning if the velocity of the movement is higher than a threshold.

Embodiments of the present disclosure further provide a (corresponding) apparatus for a surgical microscope system. The surgical microscope system comprises one or more brakes for holding at least one component of the surgical microscope system in place. The surgical microscope system comprises a surgical microscope. The apparatus comprises an interface for communicating with one or more components of the surgical microscope system. The apparatus comprises a processing module configured to obtain sensor information about a balance of the surgical microscope system from one or more sensors of the surgical microscope system. The processing module is configured to process the sensor information. The processing module is configured to determine an information about the balance of the surgical microscope system. In some embodiments, the processing module is configured to provide a warning to a user of the surgical microscope system based on the information about the balance of the surgical microscope system. The warning indicates a danger of imbalance in the surgical microscope system. Alternatively or additionally, the processing module may be configured to control a release of the one or more brakes based on the information about the balance of the surgical microscope system.

Embodiments of the present disclosure further provide a (corresponding) method for a surgical microscope system. The surgical microscope system comprises one or more brakes for holding at least one component of the surgical microscope system in place. The surgical microscope system comprises a surgical microscope. The method comprises obtaining sensor information about a balance of the surgical microscope system from one or more sensors of the surgical microscope system. The method comprises processing the sensor information. The method further comprises determining an information about the balance of the surgical microscope system. In some embodiments, the method comprises providing a warning to a user of the surgical microscope system based on the information about the balance of the surgical microscope system. The warning indicates a danger of imbalance in the surgical microscope system. Alternatively or additionally, the method may comprise controlling a release of one or more brakes based on the information about the balance of the surgical microscope system.

Embodiments of the present disclosure further provide a (corresponding) computer program with a program code for performing the method when the computer program is executed on a processor.

SHORT DESCRIPTION OF THE FIGURES

Figure 2:
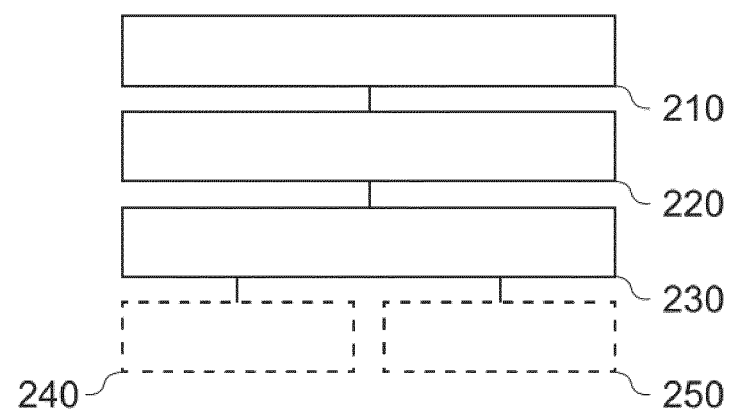
Figure 3:
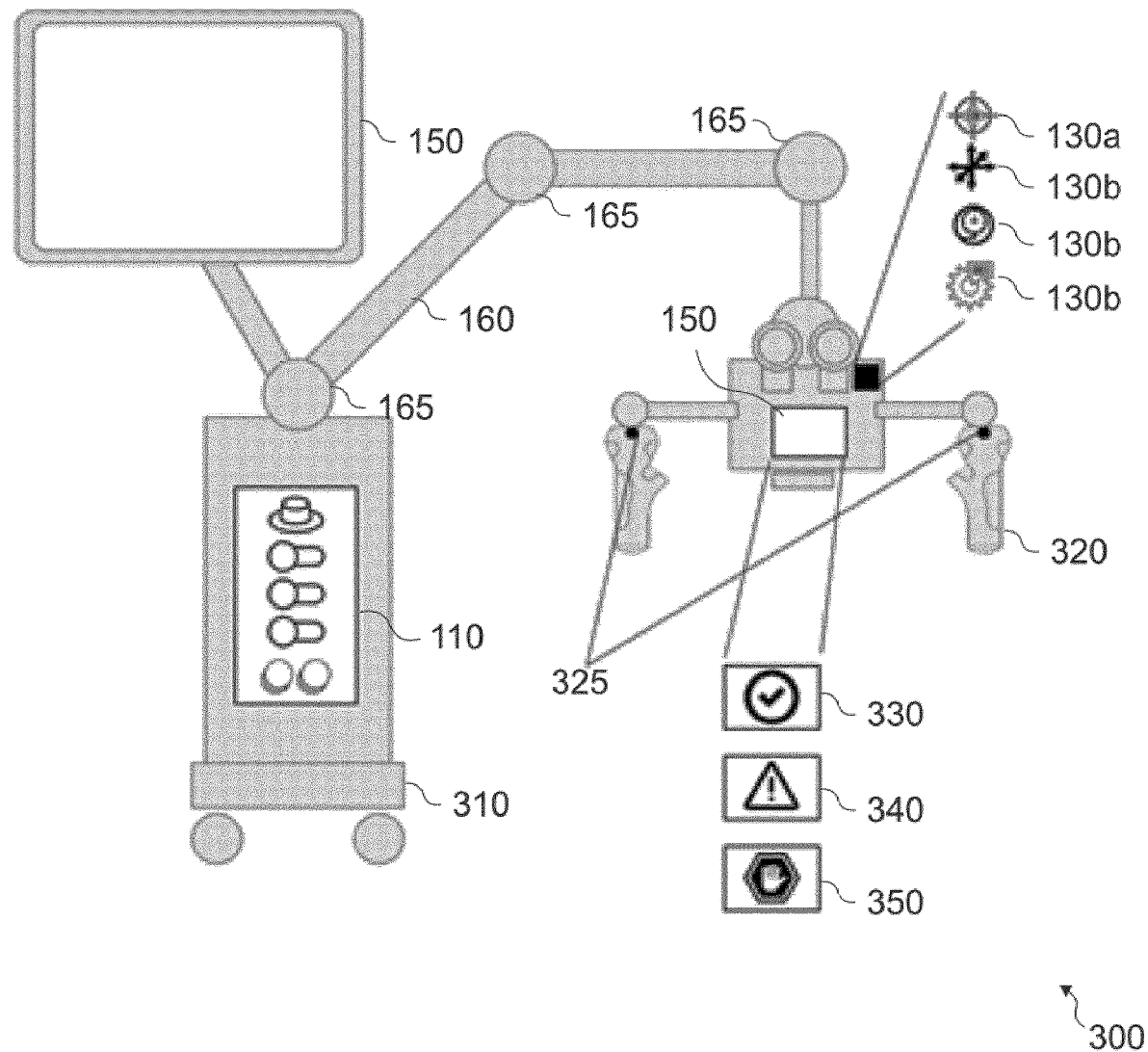

Some examples of apparatuses and/or methods will be described in the following by way of example only, and with reference to the accompanying figures, in which FIG. 1 shows a schematic block diagram of a surgical microscope system and of an apparatus for a surgical microscope system;

FIG. 2 shows a flow chart of an embodiment of a method for a surgical microscope system; and FIG. 3 shows a further block diagram of an embodiment of a surgical microscope system.

DETAILED DESCRIPTION

Various examples will now be described more fully with reference to the accompanying drawings in which some examples are illustrated. In the figures, the thicknesses of lines, layers and/or regions may be exaggerated for clarity.

Accordingly, while further examples are capable of various modifications and alternative forms, some particular examples thereof are shown in the figures and will subsequently be described in detail. However, this detailed description does not limit further examples to the particular forms described. Further examples may cover all modifications, equivalents, and alternatives falling within the scope of the disclosure. Same or like numbers refer to like or similar elements throughout the description of the figures, which may be implemented identically or in modified form when compared to one another while providing for the same or a similar functionality.

It will be understood that when an element is referred to as being "connected" or "coupled" to another element, the elements may be directly connected or coupled or via one or more intervening elements. If two elements A and B are combined using an "or", this is to be understood to disclose all possible combinations, i.e. only A, only B as well as A and B, if not explicitly or implicitly defined otherwise. An alternative wording for the same combinations is "at least one of A and B" or "A and/or B". The same applies, mutatis mutandis, for combinations of more than two Elements.

The terminology used herein for the purpose of describing particular examples is not intended to be limiting for further examples. Whenever a singular form such as "a," "an" and "the" is used and using only a single element is neither explicitly or implicitly defined as being mandatory, further examples may also use plural elements to implement the same functionality. Likewise, when a functionality is subsequently described as being implemented using multiple elements, further examples may implement the same functionality using a single element or processing entity. It will be further understood that the terms "comprises," "comprising," "includes" and/or "including," when used, specify the presence of the stated features, integers, steps, operations, processes, acts, elements and/or components, but do not preclude the presence or addition of one or more other features, integers, steps, operations, processes, acts, elements, components and/or any group thereof.

Unless otherwise defined, all terms (including technical and scientific terms) are used herein in their ordinary meaning of the art to which the examples belong.

FIG. 1 shows a schematic block diagram of a surgical microscope system 100. The surgical microscope system 100 comprises one or more sensors 120 for providing sensor information about a balance of the surgical microscope system 100. The surgical microscope system 100 comprises one or more brakes 165 for holding at least one component of the surgical microscope system in place. The surgical microscope system 100 comprises a surgical microscope 170.

Optionally, the surgical microscope system may comprise an arm 160. The arm 160 may comprise two or more components, which are separated by one or more hinges, which allow for a flexible positioning of the arm 160. The surgical microscope 170 may be attached to the arm 160. For example, at least one of the one or more brakes may be a brake for the arm 160, e.g. part of a hinge of the arm. Accordingly, the one or more brakes may be suitable for holding the arm 160 of the surgical microscope system in place. Optionally, the surgical microscope system may further comprise an output module 130. The surgical microscope system may further comprise an illumination 140 and/or a video display 150.

The surgical microscope system 100 comprises a processing module 114, which is coupled to the one or more sensors, and, optionally to at least one of the one or more brakes, the output module, the illumination, and the video display, e.g. via an interface 112. FIG. 1 further shows an apparatus 110 comprising the processing module 114 and the interface 112, which is coupled to the processing module 114. For example, the apparatus may be suitable for controlling the surgical microscope system, e.g. the apparatus 110 may be a control apparatus of the surgical microscope system. The processing module 114 is configured to process the sensor information. The processing module is configured to determine an information about the balance of the surgical microscope system 100. In some embodiments, the processing module is configured to provide a warning to a user of the surgical microscope system 100 based on the information about the balance of the surgical microscope system 100. The warning indicates a danger of imbalance in the surgical microscope system 100. Alternatively or additionally, the processing module may be configured to control a release of the one or more brakes based on the information about the balance of the surgical microscope system 100.

Embodiments of the present disclosure relate to an surgical microscope system, or to an apparatus, method or computer program for a surgical microscope system. In general, a microscope is an optical instrument that is suitable for examining objects that are too small to be examined by the human eye (alone). For example, a microscope may provide an optical magnification of an object, such as the sample of organic tissue. A surgical microscope is a microscope that is used during surgery, i.e. a microscope that is suitable for use (by a surgeon) during surgery. Such surgical microscope systems often comprise an arm or a positioning means that is used to position the surgical microscope as desired by the surgeon, e.g. close to the operating space, so the surgical microscope can be used to provide a magnified view of the wound tract or tissue. Such arms or positioning means are usually adapted to provide a wide variety of different positions and/or angles, in order to provide the surgeon with enough space to conduct the surgery, while providing the magnified image of the site of the surgery. Additionally, the arms or positioning means of surgical microscope system are often designed so they allow for easy positioning of the surgical microscope, e.g. using weights and counter-weights, using pneumatic systems or using motors to support the movement of the arm or positioning means of the surgical microscope system. As the movement is often supported by such support systems, the surgeon might not "feel" when the surgical microscope system is getting out of balance, e.g. when the surgical microscope is shifted to a position where a leverage effect is too large to be compensated by the surgical microscope system. Embodiments of the present disclosure may detect such situations and provide an advance warning or mitigate the impending imbalance. This is especially of value if one or more additional devices, such as monitors or additional cameras, are attached to the surgical microscope 170.

The surgical microscope system 100 comprises one or more sensors 120 for providing sensor information about a balance of the surgical microscope system 100. The one or more sensors may be used to detect indicators of an impending imbalance. For example, the one or more sensors 120 comprise one or more elements of the group of one or more torque sensors, one or more weight sensors, one or more accelerometers, one or more position sensors, one or more angular sensors, and one or more rotation sensors (e.g. implemented by a gyroscope). The one or more angular sensors and/or the one or more rotation sensors may be included in one or more components of the arm 160. For example, the one or more torque sensors may be used to provide information on a torque experienced at one or more hinges of the arm 160. Accordingly, the sensor information about the balance of the surgical microscope system 100 may comprise sensor information about the torque experienced at one or more hinges of the arm 160. For example, the one or more position sensor may be used to provide information about a current position of the surgical microscope 170 and/or information about a current position or orientation of one or more components of the arm 160. The one or more angular sensors and/or one or more rotation sensors may be used for a similar purpose, to provide information about a current position of the surgical microscope 170 and/or information about a current position or orientation of one or more components of the arm 160. Accordingly, the sensor information about the balance of the surgical microscope may comprise information about a current position of the surgical microscope 170 and/or information about a current position or orientation of one or more components of the arm 160. For example, the one or more accelerometers may be used to provide information about a movement of one or more components of the arm and/or information about a vibration of the arm (being caused by an imbalance of the surgical microscope system). Accordingly, the sensor information about the balance of the surgical microscope may comprise information about a movement of one or more components of the arm and/or information about a vibration of the arm. For example, the one or more weight sensors may be used to determine information about a weight of the surgical microscope (including devices attached to the surgical microscope). Accordingly, the sensor information about the balance of the surgical microscope may comprise about the weight of the surgical microscope. As indicated above, multiple sensors or types of sensors may be used. Accordingly, the sensor information about the balance of the surgical microscope system 100 may comprise sensor information from one or more different types of sensors.

The processing module 114 is configured to process the sensor information, in order to determine the information about the balance of the surgical microscope system 100. For example, the processing module 114 may be configured to scan the sensor information for indicators of an impending imbalance. For example, the processing module 114 may be configured to detect a torque that exceeds a torque threshold. If the torque threshold is exceeded, the surgical microscope system may be in danger of imbalance. For example, the processing module may be configured to detect a positioning of the surgical microscope or of one or more components of the arm that carries a heightened risk of imbalance. The positioning of the arm might carry a heightened risk of imbalance if the weight of the surgical microscope exceeds a weight threshold. If such a positioning is detected, the surgical microscope system may be in danger of imbalance. For example, the processing module may be configured to detect a vibration of the arm that exceeds a vibration threshold. This may indicate, e.g. in addition to a positioning of the surgical microscope or of one or more components of the arm that carries a heightened risk of imbalance, that the surgical microscope system is in danger of imbalance. For example, the processing module may be configured to detect a movement (e.g. a velocity of a movement) of the arm that exceeds a velocity threshold. In other words, determining the information about the balance of the surgical microscope system 100 may comprise determining a velocity of a movement of the arm 160. In this case, an actual imbalance may be detected. Again, multiple indicators may be combined to make the determination on whether the surgical microscope system is in danger of imbalance (or has already reached a state of imbalance).

In general, the information about the balance of the surgical microscope system may indicate whether (or that) the surgical microscope system 100 is in danger of losing its balance. The danger of losing balance may be conditional in this case—for example, the information about the balance of the surgical microscope system may indicate that the surgical microscope system 100 is in danger of losing its balance if the one or more brakes are released, if a position of the surgical microscope is changed by more than a threshold, if an additional weight is added to the surgical microscope etc. In some embodiments, the information about the balance may comprise a binary indication about an impending imbalance—for example, the information about the balance may provide a "true" value if the surgical microscope system is in danger of imbalance, and a "false" value if the surgical microscope system is not in danger of imbalance. Alternatively, a ternary information may be provided—with a first severity level indicating that the surgical microscope system is in balance, a second severity level indicating that the surgical microscope system is slightly imbalanced, and a third severity level indicating that the surgical microscope system is severely imbalanced. Additionally, the information about the balance of the surgical microscope system may comprise information about a source of an imbalance or information about a suitable remedy for avoiding or remedying the imbalance.

There are different options that can be chosen with regards to when the information on the balance is determined. In some cases, the information on the balance may be determined when the danger of imbalance is greatest, e.g. when the one or more brakes are released. In other words, the processing module 114 may be configured to determine the information about the balance of the surgical microscope system 100 in response to a release of one or more brakes of the surgical microscope system 100, e.g. in response to a received command related to the release of the brakes. For example, the release of the brakes may be delayed until after the determination of the information on the balance of the surgical microscope system. For example, the brakes might only be released if the risk of imbalance is smaller than a threshold. Alternatively, the brakes might be released after provision of a warning, or with a safeguard that reasserts the brakes in case of a sudden movement of the surgical microscope.

Alternatively, the information on the balance of the surgical microscope system may be constantly (e.g. periodically) updated, e.g. in order to detect changes in the balance that are due to external weights or loads being put on the surgical microscope system, or in order to detect a rolling movement of the surgical microscope system. In other words, the processing module 114 may be configured to continuously determine the information about the balance of the surgical microscope system 100.

In some embodiments, a warning may be provided to a user of the surgical microscope system (e.g. a surgeon) based on the information about the balance of the surgical microscope system 100. For example, the warning may be provided to the user if the surgical microscope system is out of balance, is in danger of imbalance, and/or to warn the user of an action that would/could cause the imbalance. Accordingly, the warning indicates the danger of imbalance in the surgical microscope system 100. In some embodiments, the warning may merely indicate that there is general danger of imbalance, e.g. without providing specifics on the source of the imbalance. In this case, the user may simply take more care when releasing the brakes of the surgical microscope system. Alternatively, the warning may indicate one or more sources of the (impending) imbalance, or one or more courses of action to take to avoid or remedy the imbalance. Additionally or alternatively, in the warning, two or more severity levels may be distinguished, e.g. a first severity level warning of a minor imbalance, and a second severity level warning of a danger due to a major imbalance. The warning may indicate the severity level (e.g. through different colors (yellow and red), different descriptions or symbols, or different pictograms). In some embodiments, a third severity level indicating a balanced state of the surgical microscope system may also be indicated, e.g. in the form of a green light or an affirmative pictogram.

In general, the warning may be provided via one or more different means, e.g. visual, audio or tactile means. The warnings may, thus, use employ one or more components of the surgical microscope system. For example, the surgical microscope system may comprise an output module 130 for providing the warning for a user of the surgical microscope system 100. The warning may be provided via the output module 130.

For example, the warning may be provided as, or comprise, a visual warning. Accordingly, the output module may comprise a light (e.g. a light-emitting diode) or a display (e.g. a video display or a status display). Alternatively, existing visual output modules may be repurposed to provide the visual warning. For example, the processing module 114 may be configured to dim, modulate (e.g. pulse) or deactivate an illumination 140 (e.g. a spot illumination of the patient, or a background illumination) or a video display 150 of the surgical microscope system 100 as warning for the user of the surgical microscope system 100. For example, the video display may be a display of a (digital) viewfinder of the surgical microscope system, or of an overview display of the surgical microscope system.

Alternatively or additionally, the warning may be or comprise an audio or auditory warning, i.e. provided as an audio warning. Accordingly, the output module 130 may comprise an audio output module. For example, the warning may be provided as an alarm sound, or as a spoken text providing a warning message or an instruction message. A sound intensity, frequency, and repetition rate of the audio warning may be indicative of the severity of the imbalance.

Both (or either) the visual and the audio warning may be used to provide instructions to the user of the surgical microscope system, e.g. to be careful in operating the surgical microscope system, or specific instruction as to how the surgical microscope is to be moved to achieve a balanced state. Additionally or alternatively, the warnings may relate to the auto-balancing function. For example, the surgical microscope system 100 may comprise an auto-balancing system for balancing the surgical microscope system 100. The warning may request the user to initiate the auto-balancing system. Different options are possible, depending on parameters such as the severity of imbalance, and user preferences. In some embodiments, the warning may suggests to the user to initiate the auto-balance process. For example, the request may be provided as a visual or as an audio/auditory warning. Alternatively, the user may be forced to initiate the auto-balance process, e.g. by not allowing to release the brakes, or switching off other microscope functions such as illumination or video. In some embodiments, the auto-balance might be automatically performed, e.g. as soon as the processing module assumes that the user has finished adjusting the arm.

Alternatively or additionally, the warning may be provided as a haptic feedback. For example, the output module 130 may comprise a haptic feedback actuator, e.g. a vibration module. The haptic feedback actuator may, for example, be integrated in the handles of the surgical microscope. Accordingly, the warning be provided as haptic feedback, e.g. as vibration feedback.

Alternatively or additionally, the one or more brakes may be controlled (by the processing module) in order to avoid or limit a sudden movement of the surgical microscope. The surgical microscope system 100 comprises the one or more brakes 165 that are suitable for, or configured to, holding/hold at least one component of the surgical microscope system in place. For example, the one or more brakes may be suitable for, or configured to, hold the entire surgical microscope system in place. For example, the one or more brakes may be or comprise one or more brakes for braking one or more wheels of the surgical microscope system, e.g. one or more wheels for moving the (entire) surgical microscope system on the floor. In some embodiments, only a component of the surgical microscope system may be held in place, e.g. via the arm 160 or positioning means of the surgical microscope system. For example, the one or more brakes 165 may be suitable for holding the arm 160 in place. For example, the one or more brakes 165 may be or comprise one or more brakes that are suitable for, or configured to, hold the arm 160 of the surgical microscope system 100 in place. These brakes may be released when the surgical microscope 170 is to be moved. Once the one or more brakes are released, a positioning or orientation of the arm 160 may be adjustable, enabling a change in the position of the surgical microscope 170 that is attached to the arm 160. In at least some embodiments, the brakes may be released using one or more buttons that are arranged at one or more handles of the surgical microscope. Once the buttons are released, the brakes may be (re-)asserted.

The processing module may be configured to control the release of the one or more brakes based on the information about the balance of the surgical microscope system 100. For example, the processing module may be configured to override a control of the one or more brakes based on the information on the balance of the surgical microscope system. If the information on the balance of the surgical microscope system indicates a danger of imbalance, the processing module may be configured to limit the operation of the brakes, e.g. in order to re-engage the brakes if the surgical microscope moves more than a pre-defined distance downwards, or in order to limit an positioning of the surgical microscope away from the patient. For examples, the brake override may be complete, i.e. the brake-release button may become inactive, or partial, i.e. the brakes might only be released partially so that fast or big movements are prevented, or temporary, e.g. the brakes may be released but re-engaged after some time or movement, e.g. after 0.1 seconds, or 1 cm of movement, so that the user is informed about the situation but potentially dangerous situations may be prevented. In other words, the processing module 114 may be configured to at least partially (e.g. so the one or more brakes might not fully open and allow an operation with more force required to move the surgical microscope) and/or temporarily (e.g. until a warning is provided, or in short time or distance increments) block a release of the one or more brakes based on the information about the balance of the surgical microscope system 100, e.g. if the information on the balance of the surgical microscope system indicates a danger of imbalance. For example, the release of the one or more brakes may be initiated or triggered by the user. Consequently, the processing module may be configured to control, limit, block and/or override the user-initiated release of the one or more brakes. Should the user decide that the imbalance is not too severe and decide to continue, e.g. by continuing pressing the brake-release button, the system may eventually, after a few one or more iterations of brake activation-deactivations, allow the user to release the brakes.

The interface 112 may correspond to one or more inputs and/or outputs for receiving and/or transmitting information, which may be in digital (bit) values according to a specified code, within a module, between modules or between modules of different entities. For example, the interface 12 may comprise interface circuitry configured to receive and/or transmit information. In embodiments the processing module 114 may be implemented using one or more processing units, one or more processing devices, any means for processing, such as a processor, a computer or a programmable hardware component being operable with accordingly adapted software. In other words, the described function of the processing module 114 may as well be implemented in software, which is then executed on one or more programmable hardware components. Such hardware components may comprise a general purpose processor, a Digital Signal Processor (DSP), a micro-controller, etc.

More details and aspects of the surgical microscope system or the apparatus for the surgical microscope system are mentioned in connection with the proposed concept or one or more examples described above or below (e.g. FIG. 2 or 3). The surgical microscope system or the apparatus for the surgical microscope system may comprise one or more additional optional features corresponding to one or more aspects of the proposed concept or one or more examples described above or below.

FIG. 2 shows a flow chart of an embodiment of a (corresponding) method for a surgical microscope system. For example, the surgical microscope system may be implemented similar to the surgical microscope system of FIG. 1. The method comprises obtaining 210 sensor information about a balance of the surgical microscope system 100 from one or more sensors 120 of the surgical microscope system 100. The method comprises processing 220 the sensor information. The method comprises determining 230 information about the balance of the surgical microscope system 100. In some embodiments, the method comprises providing 240 a warning to a user of the surgical microscope system 100 based on the information about the balance of the surgical microscope system 100. The warning indicates a danger of imbalance in the surgical microscope system 100. Additionally or alternatively, the method may comprise controlling 250 a release of one or more brakes based on the information about the balance of the surgical microscope system 100.

As indicated above, features described in connection with the surgical microscope system 100 of FIG. 1 may be likewise applied to the method of FIG. 2.

More details and aspects of the method are mentioned in connection with the proposed concept or one or more examples described above or below (e.g. FIGS. 1 or 3). The method may comprise one or more additional optional features corresponding to one or more aspects of the proposed concept or one or more examples described above or below.

At least some embodiments relate to a safety of a microscope balance. Embodiments may provide a technical approach for avoiding situations where the microscope moves abruptly due to imbalance At least some embodiments may enable the microscope to assess the balance condition, and automatically take actions to prevent risky situations.

FIG. 3 shows a further block diagram of an embodiment of a surgical microscope system 300. The surgical microscope system comprises a base unit 310, a control apparatus 110, an arm 160 with three brakes 165 that are integrated in the hinges of the arm 160, a surgical microscope 170, and two displays 150—one display located near the eyepiece, and another, larger display. Two handles 320 are attached to the surgical microscope 170, each of the handles comprising a brake-release button 325. The surgical microscope system 300 further comprises sensors 130a to 130b.

Assessment of the balance condition (e.g. the determination of the information on the balance of the surgical microscope system) can be done in various ways:

For example, the balance condition may be assessed by means of sensors such as torque sensors 130d, and weight sensors 130c, or combination of them. They could provide continuous measurement of the balance conditions while the microscope is not used.

Alternatively or additionally, the balance condition may be assessed by performing very fast measurements of the movements upon the release of the arm brakes. This can be done by means of sensors such as accelerometers 130b, or position/rotation sensors (such as a gyroscope 130a). Technically, a degree of imbalance might not be detected, but rather how fast the microscope moves. If this assessment is done fast enough, it may provide a more direct assessment of the risk. The measurements may be done within milliseconds, and if the microscope is moving too fast, the brakes may be reactivated fast.

The information of the balance condition (i.e. the information on the balance of the surgical microscope system) may be used to trigger different actions:

For example, a warning may provided be in any combination of the following forms:

A visual indication/warning may be shown, e.g. red light/sign for imbalanced, green for balanced microscope, or via a display 150. At reference sign 330, a pictogram displayed by one of the displays is shown, the pictogram indicating that the balancing state is ok, and that the surgical microscope system is balanced. At reference sign 340, a warning pictogram is shown, indicating a minor imbalance. At reference sign 350, a danger pictogram is shown, indicating a major imbalance.

An audio warning may be given. A sound intensity, frequency, and repetition rate of the audio warning may be indicative of the severity of the imbalance.

Haptic feedback (vibration) may be given to warn the user, e.g. when the user touches the handle 320, or the brake release button 325.

Other microscope functions may be adjusted. For example, an illumination may be reduced or turned off, or a video display may be dimmed or switched off.

Additionally or alternatively, the user's command to release the brakes may be overridden. This override may be complete, i.e. the brake-release button may become inactive, partial, i.e. the brakes might only be released partially so that fast or big movements are prevented, or temporary, e.g. the brakes may be released but re-engaged after some time or movement, e.g. after 0.1 seconds, or 1 cm of movement, so that the user is informed about the situation but potentially dangerous situations may be prevented. Should the user judge that the imbalance is not severe enough and wants to continue, and continues pressing the brake-release button, the system may eventually, after a few iteration of activation-deactivations, allow the user to release the brakes.

In some embodiments, the surgical microscope system may act towards auto-balance function. Different options are possible, depending on parameters such as the severity of imbalance, and user preferences:

The auto-balance may be automatically performed. For example, when the balance is disturbed, and the user is not holding the handles, and after the lapse of a predetermined time, e.g. 10 seconds, the microscope could assume that the user has finished a current change, indicating that there is the opportunity to rebalance.

Suggest to the user to initiate the auto-balance process, e.g. as part of a warning Force the user to initiate the auto-balance process, by not allowing to release the brakes, or switching off other microscope functions such as illumination or video.

As used herein the term "and/or" includes any and all combinations of one or more of the associated listed items and may be abbreviated as "/".

Although some aspects have been described in the context of an apparatus, it is clear that these aspects also represent a description of the corresponding method, where a block or device corresponds to a method step or a feature of a method step. Analogously, aspects described in the context of a method step also represent a description of a corresponding block or item or feature of a corresponding apparatus. Some or all of the method steps may be executed by (or using) a hardware apparatus, like for example, a processor, a microprocessor, a programmable computer or an electronic circuit. In some embodiments, some one or more of the most important method steps may be executed by such an apparatus.

Depending on certain implementation requirements, embodiments of the invention can be implemented in hardware or in software. The implementation can be performed using a non-transitory storage medium such as a digital storage medium, for example a floppy disc, a DVD, a Blu-Ray, a CD, a ROM, a PROM, and EPROM, an EEPROM or a FLASH memory, having electronically readable control signals stored thereon, which cooperate (or are capable of cooperating) with a programmable computer system such that the respective method is performed. Therefore, the digital storage medium may be computer readable.

Some embodiments according to the invention comprise a data carrier having electronically readable control signals, which are capable of cooperating with a programmable computer system, such that one of the methods described herein is performed.

Generally, embodiments of the present invention can be implemented as a computer program product with a program code, the program code being operative for performing one of the methods when the computer program product runs on a computer. The program code may, for example, be stored on a machine readable carrier.

Other embodiments comprise the computer program for performing one of the methods described herein, stored on a machine readable carrier.

In other words, an embodiment of the present invention is, therefore, a computer program having a program code for performing one of the methods described herein, when the computer program runs on a computer.

A further embodiment of the present invention is, therefore, a storage medium (or a data carrier, or a computer-readable medium) comprising, stored thereon, the computer program for performing one of the methods described herein when it is performed by a processor. The data carrier, the digital storage medium or the recorded medium are typically tangible and/or non-transitionary. A further embodiment of the present invention is an apparatus as described herein comprising a processor and the storage medium.

A further embodiment of the invention is, therefore, a data stream or a sequence of signals representing the computer program for performing one of the methods described herein. The data stream or the sequence of signals may, for example, be configured to be transferred via a data communication connection, for example, via the internet.

A further embodiment comprises a processing means, for example, a computer or a programmable logic device, configured to, or adapted to, perform one of the methods described herein.

A further embodiment comprises a computer having installed thereon the computer program for performing one of the methods described herein.

A further embodiment according to the invention comprises an apparatus or a system configured to transfer (for example, electronically or optically) a computer program for performing one of the methods described herein to a receiver. The receiver may, for example, be a computer, a mobile device, a memory device or the like. The apparatus or system may, for example, comprise a file server for transferring the computer program to the receiver.

In some embodiments, a programmable logic device (for example, a field programmable gate array) may be used to perform some or all of the functionalities of the methods described herein. In some embodiments, a field programmable gate array may cooperate with a micro-processor in order to perform one of the methods described herein. Generally, the methods are preferably performed by any hardware apparatus.

LIST OF REFERENCE SIGNS

100 Surgical microscope system
110 Apparatus for a surgical microscope system
112 Interface
114 Processing module
120 One or more sensors
130 Output module
130a Gyroscope
130b Accelerometer
130c Weight sensor
140c Torque sensor
140 Illumination
150 Display
160 Arm
165 Brakes
170 Surgical Microscope
210 Obtaining sensor information
220 Processing the sensor information
230 Determining information about a balance of a surgical microscope system
240 Providing a warning
250 Controlling a release of one or more brakes
300 Surgical microscope system
310 Base unit
320 Handles
325 Brake-release button
330 Display—OK—Balanced
340 Display—Warning—Minor Imbalance
350 Display—Danger—Major Imbalance

What is claimed is:

1. A surgical microscope system comprising:
one or more sensors for providing sensor information about a balance of the surgical microscope system;
one or more brakes for holding at least one component of the surgical microscope system in place;
a surgical microscope; and
a processing module, configured to:
process the sensor information,
determine an information about the balance of the surgical microscope system, and
control a release of the one or more brakes based on the information about the balance of the surgical microscope system by overriding a control of the one or more brakes based on the information on the balance of the surgical microscope system or by limiting operation of the brakes if the balance of the surgical microscope system indicates a danger of imbalance.

2. The surgical microscope system according to claim 1, wherein the processing module is configured to determine the information about the balance of the surgical microscope system in response to a release of one or more brakes of the surgical microscope system.

3. The surgical microscope system according to claim 1, wherein the processing module is configured to continuously determine the information about the balance of the surgical microscope system.

4. The surgical microscope system according to claim 1, wherein the processing module is further configured to provide a warning to a user of the surgical microscope system based on the information about the balance of the surgical microscope system, the warning indicating a danger of imbalance in the surgical microscope system, the surgical microscope system comprising an output module for providing the warning for a user of the surgical microscope system, the warning being provided via the output module.

5. The surgical microscope system according to claim 4, wherein the output module comprises a light or a display, wherein the warning is provided as a visual warning, and/or wherein the output module comprises an audio output module, wherein the warning is provided as an audio warning.

6. The surgical microscope system according to claim 4, wherein the output module comprises a haptic feedback actuator, wherein the warning is provided as haptic feedback.

7. The surgical microscope system according to claim 1, wherein the processing module is configured to dim or deactivate an illumination or a video display of the surgical microscope system as warning for the user of the surgical microscope system based on the information about the balance of the surgical microscope system, the warning indicating a danger of imbalance in the surgical microscope system.

8. The surgical microscope system according to claim 1, wherein the processing module is configured to at least partially and/or temporarily block a release of the one or more brakes based on the information about the balance of the surgical microscope system.

9. The surgical microscope system according to claim 1, wherein the surgical microscope system comprises an auto-balancing system for balancing the surgical microscope system, and the processing module is further configured to provide a warning to a user of the surgical microscope system based on the information about the balance of the surgical microscope system, the warning indicating a danger of imbalance in the surgical microscope system, wherein the warning requests the user to initiate the auto-balancing system.

10. The surgical microscope system according to claim 1, wherein the one or more sensors comprise one or more elements of the group of one or more torque sensors, one or more weight sensors, one or more accelerometers, one or more position sensors, one or more angular sensors, one or more rotation sensors.

11. The surgical microscope system according to claim 1, comprising an arm, wherein the one or more brakes are suitable for holding the arm in place, wherein the surgical microscope is attached to the arm.

12. The surgical microscope system according to claim 11, wherein determining the information about the balance of the surgical microscope system comprises determining a velocity of a movement of the arm.

13. An apparatus for a surgical microscope system, the surgical microscope system comprising one or more brakes for holding at least one component of the surgical microscope system in place, and a surgical microscope, the apparatus comprising:
an interface for communicating with one or more components of the surgical microscope system; and
a processing module configured to:
obtain sensor information about a balance of the surgical microscope system from one or more sensors of the surgical microscope system,
process the sensor information,
determine an information about the balance of the surgical microscope system, and
control a release of the one or more brakes based on the information about the balance of the surgical microscope system by overriding a control of the one or more brakes based on the information on the balance of the surgical microscope system or by limiting operation of the brakes if the balance of the surgical microscope system indicates a danger of imbalance.

14. A method for a surgical microscope system, the surgical microscope system comprising one or more brakes for holding at least one component of the surgical microscope system in place, and a surgical microscope, the method comprising:
obtaining sensor information about a balance of the surgical microscope system from one or more sensors of the surgical microscope system;
processing the sensor information;
determining an information about the balance of the surgical microscope system; and
controlling a release of one or more brakes based on the information about the balance of the surgical microscope system by overriding a control of the one or more brakes based on the information on the balance of the surgical microscope system or by limiting operation of the brakes if the balance of the surgical microscope system indicates a danger of imbalance.

15. A non-transitory, computer-readable medium comprising a program code that, when the program code is executed on a processor, a computer, or a programmable hardware component, causes the processor, computer, or programmable hardware component to perform the method of claim 14.

* * * * *